US006851459B2

(12) United States Patent
Squirrell et al.

(10) Patent No.: US 6,851,459 B2
(45) Date of Patent: Feb. 8, 2005

(54) AIR SAMPLERS

(75) Inventors: David James Squirrell, Salisbury (GB); William Hunter Symonds, Salisbury (GB); Hilary Anne Bird, Salisbury (GB); Martin John Berry, Salisbury (GB)

(73) Assignee: The Secretary of State for Defence in Her Britannic Majesty's Government of the United Kingdom of Great Britain and Northern Ireland (GB)

( * ) Notice: Subject to any disclaimer, the term of this patent is extended or adjusted under 35 U.S.C. 154(b) by 140 days.

(21) Appl. No.: 10/381,947

(22) PCT Filed: Oct. 1, 2001

(86) PCT No.: PCT/GB01/04387

§ 371 (c)(1), (2), (4) Date: Mar. 31, 2003

(87) PCT Pub. No.: WO02/29380

PCT Pub. Date: Apr. 11, 2002

(65) Prior Publication Data

US 2004/0025963 A1 Feb. 12, 2004

(30) Foreign Application Priority Data

Oct. 4, 2000 (GB) .......................................... 00242271

(51) Int. Cl.[7] ................................................ B65B 1/20

(52) U.S. Cl. ............................ 141/70; 141/83; 141/94; 141/197; 73/863.21; 73/863.83; 73/864.34; 73/864.81

(58) Field of Search ............................. 141/18, 69, 70, 141/83, 94, 192, 197; 73/863, 863.21, 863.71, 863.83, 864, 864.34, 864.81

(56) References Cited

U.S. PATENT DOCUMENTS

| | | | | |
|---|---|---|---|---|
| 5,154,891 A | | 10/1992 | Brenner | |
| 5,621,180 A | * | 4/1997 | Simon et al. | 73/864.52 |
| 6,550,347 B2 | * | 4/2003 | Bradley | 73/863.21 |
| 6,553,848 B1 | * | 4/2003 | Tallentire et al. | 73/864.81 |

FOREIGN PATENT DOCUMENTS

| | | |
|---|---|---|
| EP | 0213031 | 3/1987 |
| EP | 0668095 | 8/1995 |
| EP | 0927578 | 7/1999 |

* cited by examiner

*Primary Examiner*—Timothy L. Maust
(74) *Attorney, Agent, or Firm*—Dean W. Russell; Kilpatrick Stockton LLP

(57) ABSTRACT

An air sampler for use in analyzing biological or other analytes, comprizes an airflow chamber having an air inlet and an air outlet. An extract from an air mover draws ambient air in through the inlet, and then through the chamber, to discharge it back to atmosphere by way of an outlet. The airflow chamber houses a cyclone air/liquid separator through which the inflowing air is caused to pass. An injector introduces liquid into air flowing through the air inlet. The cyclone separator extracts this liquid and any entrained particles therein and discharges it from the airflow chamber, initially by way of a duct, where it is then conveyed to a collection vessel, by way of a three channel peristaltic pump, and a duct. The collection vessel is housed within a Peltier-cooled holder to maintain the contents of the vessel within the 2–8 degree Celsius range.

11 Claims, 2 Drawing Sheets

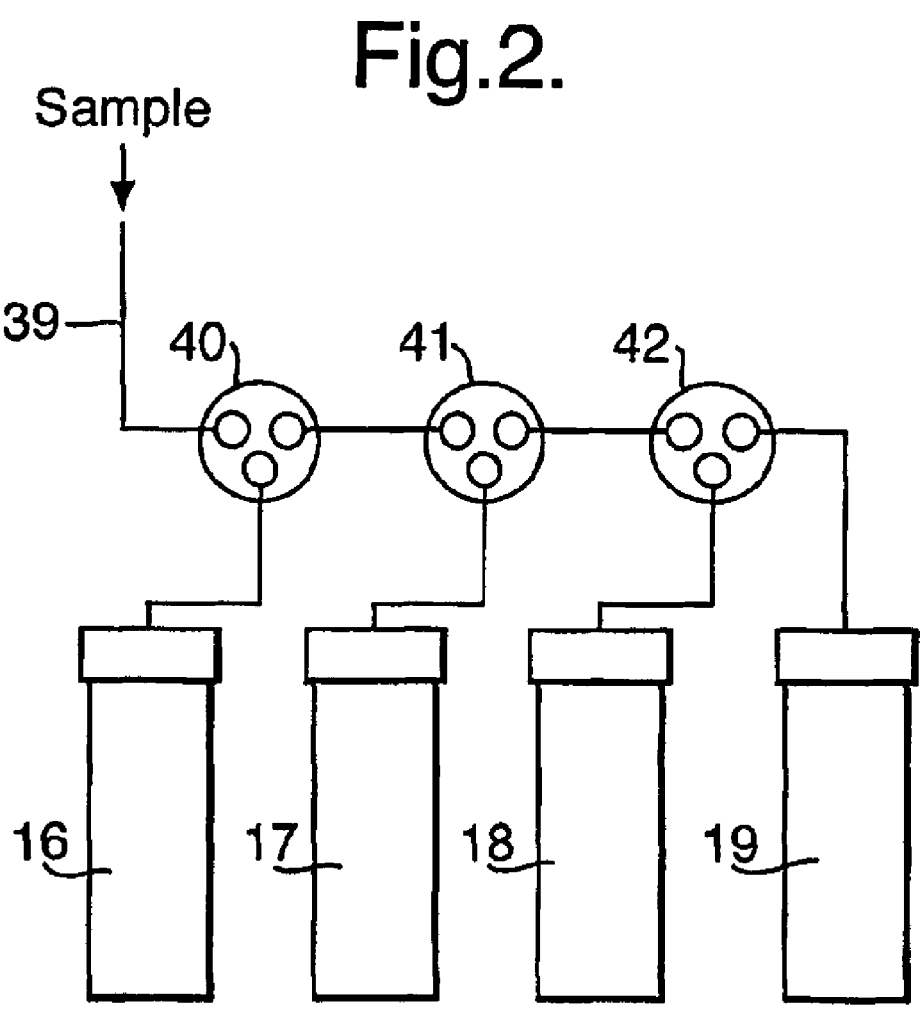

AIR SAMPLERS

CROSS REFERENCE TO RELATED APPLICATIONS

This application claims priority to Great Britain Application No. 0024227.1 filed on Oct. 4, 2000 and is the U.S. national phase of International Application No. PCT/GB01/04387 filed on Oct. 1, 2001 published in English as International Publication No. WO 02/29380 A2 on Apr. 11, 2002, the entire contents of which are hereby incorporated by reference.

This invention relates to air samplers and particularly, but not exclusively, relates to air samplers for sampling the ambient atmosphere, in order to detect and measure contamination that may be present. Air samplers are known in the art. EP-A-0 927 578 discloses a method and apparatus for sampling gaseous elements, which comprises a chamber with a gas flow inlet, outlet, and a component for dividing the gas flow into streams as it continuously flows from the inlet to the outlet. The apparatus also comprises a means for introducing entraining liquid into the chamber above the gas dividing component, a tank, and a means for continuously recirculating this entraining liquid. EP-A-0 668 095 discloses a gas liquid interface apparatus comprising a chamber where the gas and liquid interface, with each other which in turn comprises a liquid level sensor orientated to sense the presence of liquid within said chamber. Although the prior art provides different teaching on air samplers, it does not provide for an air sampler whereby cumulative samples of the entrained liquid can be isolated during use.

The present invention provides an air sampler for collecting cumulative samples from large volumes of air in small volumes of liquid, (e.g. particles from 100 cubic metres of air in about 10 mls of liquid).

In addition sequential samples may be taken automatically. These samples may be kept cool to preserve them for later analysis.

According to the present invention, an air sampler comprises an air flow chamber having an air inlet and an air outlet, means for introducing liquid into air flowing through the chamber so as to entrain any particles present in the airflow, means for collecting the entraining liquid and any entrained particles therein, and for depositing the same in a collection vessel, means for returning collected entraining liquid to the airflow chamber, means for detecting the presence of bubbles in the returning liquid, and operable to introduce fresh entraining liquid into air flowing through the airflow chamber, and means for collecting a sample of the entraining liquid and any particles therein, which may be present in said collection vessel.

An embodiment of the invention will now be described by way of example only, with reference to the accompanying drawings wherein:

FIG. 2 is an enlarged detail of part of FIG. 1.

Figure 1:
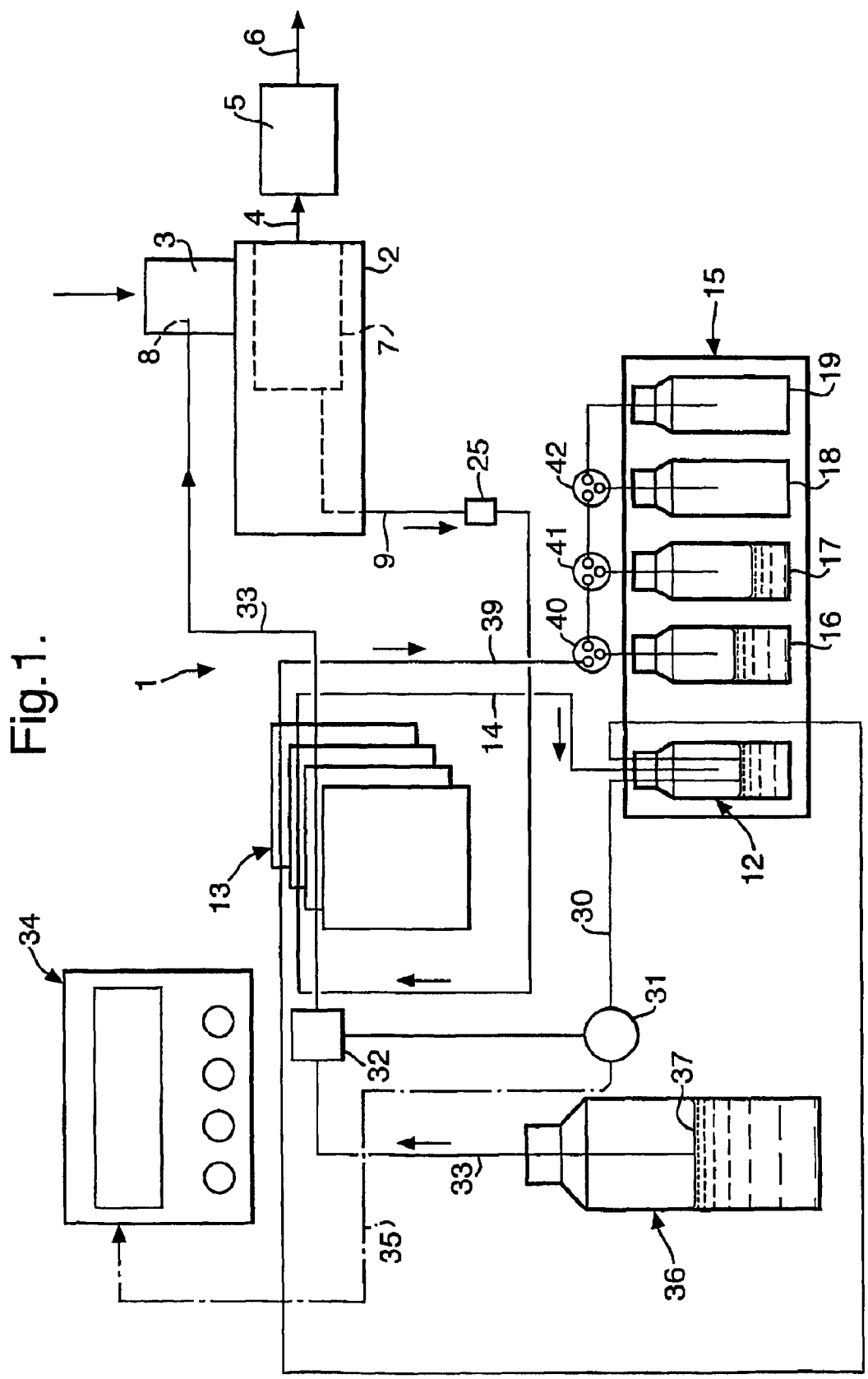
FIG. 1 is a diagrammatic illustration of the air sampler.

With reference to FIG. 1, an air sampler 1 for use in analysing biological analytes, comprises an airflow chamber 2 having an air inlet 3 and an air outlet 4.

An air mover 5, conveniently an extraction fan, draws ambient air at 500 to 1000 liters per minute in through the inlet 3, and then through the chamber 2, to discharge it back to atmosphere by way of an outlet 6.

The air flow chamber 2 houses a cyclone air/liquid separator 7 through which the inflowing air is caused to pass.

Means comprising an injector 8 introduces liquid into air flowing through the air inlet 3. The cyclone separator 7 extracts this liquid and any entrained particles therein and discharges it from the airflow chamber 2, initially by way of a duct 9, where it is then conveyed to a collection vessel 12, by way of one channel of a single three channel peristaltic pump 13 and a duct 14. The collection vessel 12 is housed within a Peltier-cooled holder 15 to maintain the contents of the vessel 12 within the 2° C.–8° C. range which is desirable for maintaining the integrity of biological analytes such as bacteria or proteins. Analyses such as PCR, (Polymerase Chain Reaction), culture or agar plates or immunoassays may be performed on the collected samples.

The holder 15 also houses bottles 16,17,18 and 19.

A large pore (e.g. 25 micron) filter unit 25 is fitted in the duct 9 to remove large particulates present in the collected air which are unsuitable for a particular assay. Diesel soot, for example. The filter unit 25 will, however, allow soluble enalytes or small particulate analytes, such as bacteria and viruses, to pass through.

The sampler 1 further comprises recirculation means for returning collected entraining liquid from the vessel 12 to the airflow chamber 2 where it is discharged to air flowing into the cyclone 7. These means comprise an extraction line 30, a bubble detector 31, a pinch valve 32, and a discharge line 33 which passes through another of the three channels of pump 13. The bubble detector 31 is connected to electronic circuitry, which includes, a programmable timer 34, by way of an electronic signal line 35. The circuitry incorporates a controlling microprocessor.

A reservoir 36 houses entrainment liquid 37, comprising de-ionised water containing 0.01% of a non-ionic detergent such as Tween-20 and 10 mM HEPES N-2-hydroxyethyl piperazine-$N^1$-2 ethane sulphonic acid buffer; pH 7.5. Line 33 draws this liquid from the reservoir 36 by way of the pinch valve 32, and passes it, via a needle-gauge stainless tube, which forms the injector 8, into the air flow inlet 3, at about 2.0 milliliters per minute.

Aerosol particles entrained into the liquid stream exit from the air flow chamber 2, (via a standard Luer-fitting port), and through pump 13, to be deposited in the collection vessel 12.

The collection fluid is re-circulated from the vessel 12 back into the airflow chamber 2 by way of line 30, bubble detector 31, pinch valve 32, pump 13 and line 33. This continues until the level of liquid within the vessel 12 falls to a point whereby air rather than liquid is drawn into line 30. When the entrained air reached the bubble detector 31, an electronic signal is sent via line 35 to the microprocessor in the electronic circuitry which includes programmable timer 34. The microprocessor then operates the pinch valve 32, so that, for a pre-set period of time, fresh collection fluid is drawn from the reservoir 36 and discharged into the airflow chamber 2, by way of line 33, pinch valve 32, pump 13, line 33 and injector 8.

After the set period the pinch valve 32 is operated so that the system is restored to the re-circulation mode, which continues until the liquid level falls again in vessel 12, and air is again entrained.

A time delay is built into the system so as to allow fluid from the re-charged vessel 12 to reach the bubble detector 31.

In addition, a start up routine is programmed into timer 34 to allow initial charging of the system.

As mentioned above, pump 13 is a single three channel pump. Two of the channels of the pump are used for pumping liquid into and out of the airflow chamber 2. The remaining channel is used to draw off small volumes of liquid for discharge to a selected one or more of the sample bottles 16, 17, 18 and 19, via line 39 and three-way valves 40, 41 and 42. (See FIG. 2).

In this example, the flow rate of entraining liquid into the airflow chamber 2 and cyclone 7 is ca.2 milliliters per minute, the sample for analysis may be drawn off at a much lower rate of ca.50 microliters per minute, using smaller bore tubing. This allows an integrated sample of aerosol particles to be collected for up to 8 hours into a standard 25 ml "universal" bottle. In the present embodiment there are four sample bottles, (16–19) so monitoring the air for an 8-hour working shift, or a full 24 hour day, is possible without the need for an operator to be present. In addition, the programmable timer 34 allows the equipment to be positioned and then to be activated automatically at set times up to one week in advance. For 4 samples, the 3-way valves (40–42) are needed to direct the sample flow.

The collected samples are subsequently analysed in the conventional manner.

What is claimed is:

1. An air sampler comprising an airflow chamber having:

(a) an air inlet;

(b) an air outlet;

(c) means for introducing liquid into air flowing through the chamber so as to entrain any particles present in the airflow;

(d) means for collecting the entraining liquid and any entrained particles therein, and for depositing the same in a collection vessel;

(e) means for returning collected entrained liquid to the airflow chamber;

(f) means for detecting the presence of bubbles in the returning liquid and which is operable to introduce fresh entraining liquid into air flowing through the airflow chamber; and (g) means for collecting a sample of the entraining liquid and any particles therein, which may be present in said collection vessel.

2. The air sampler of claim 1, provided with a programmable timer means operable to obtain air samples at predetermined times.

3. The air sampler of claim 2, incorporating a microprocessor for controlling the sampler.

4. The air sampler of claim 1, wherein said fresh entraining liquid is introduced when the level in the collection vessel falls to a level whereby air is entrained in the returned collected liquid, and is detected by said means for detecting bubbles.

5. The air sampler of claim 1, provided with a plurality of sampler bottles and means for drawing off liquid so as to divert it to the bottles.

6. The air sampler of claim 1, provided with a three channel pump and a plurality of sampler bottles, wherein two of the channels of the pump are used for pumping liquid into and out of the airflow chamber and the third channel is used to draw-off liquid and divert it to a selected sample bottle.

7. The air sampler of claim 6, wherein the pump is a single, three channel peristaltic pump.

8. The air sampler of claim 1, wherein the air sampler comprises an air mover which draws ambient air at 500 to 1000 liters per minute in through the air outlet.

9. The air sampler of claim 6, wherein the third channel is used to draw off small volumes of liquid for discharge to a selected more than one sample bottle.

10. The air sampler of claim 6, wherein the sample bottle has a volume of about 25 ml and the sample has a volume of about 10 ml.

11. The air sampler of claim 6, wherein the plurality of sample bottles are housed within a cooled holder to maintain their contents within about 2° C. to about 8° C. temperature range.

* * * * *